United States Patent [19]

Hata

[11] 3,957,974

[45] May 18, 1976

[54] METHOD FOR DEODORIZATION OF EXCREMENTS

[75] Inventor: Kosei Hata, Osaka, Japan

[73] Assignee: Seikenkai, Japan

[22] Filed: Nov. 5, 1974

[21] Appl. No.: 521,190

[52] U.S. Cl. .............................................. 424/93
[51] Int. Cl.² ........................................ A61K 35/74
[58] Field of Search ............... 426/2, 71, 342, 374, 426/805, 807; 71/12, 8–10; 424/93

[56] References Cited
UNITED STATES PATENTS

| | | | |
|---|---|---|---|
| 1,729,752 | 10/1929 | Southgate | 424/93 |
| 1,903,014 | 3/1933 | Myers | 424/93 |
| 3,274,003 | 9/1966 | Zilliken | 426/71 |

Primary Examiner—A. Louis Monacell
Assistant Examiner—R. B. Penland
Attorney, Agent, or Firm—Wenderoth, Lind & Ponack

[57] ABSTRACT

This invention is a method for deodorization of excrements which is characterized by cultivating a microorganism of Lactobacillus, said microorganism having the ability to deodorize or reduce the odor of raw excrements or a diluent thereof when cultivated with these materials, and then administering to human beings or animals the living cells of this microorganism as such or in admixture with a feed.

7 Claims, No Drawings

METHOD FOR DEODORIZATION OF EXCREMENTS

This invention relates to a method for deodorization of human beings' or animals' excrements or night soil, and especially to a harmless method of propagating a microorganism in the body of the said animals thereby enabling them to discharge excrements with no or remarkably reduced odor for a long time. More particularly, it relates to isolating and collecting a microorganism of the genus Lactobacillus which has the ability to deodorize or reduce the odor of excrements or a diluent thereof when cultivated with these materials, producing a large amount of living cells thereof by cultivation, and then administering to human beings or animals the said living cells as such as in admixture with various substances.

In the following, human beings and animals are all simply referred to as animals.

While investigating microorganisms belonging to Lactobacillus, we have found strain No. 1946/F.R.I. and a new group of Lactobacillus strains which have the ability of deodorize raw excrements or a diluent thereof when cultivated with these materials. Simultaneously, we confirmed that, when the living cells obtained by cultivating these microorganisms or a mixture thereof with a feed administered to animals, excrements discharged from said animals are free of its peculiar odor. We also confirmed that all the microorganisms such as, Strain No. 1946/F.R.I. isolated by us, and belonging to the genus Lactobacillus, remain stable in the animals' intestines, utilize or change the substances giving out the peculiar odor of excrements and are non-pathogenic. Further, from the results obtained it was presumed that the microorganisms belonging to Lactobacillus are not only non-pathogenic but also serve to bind the bowels.

The definition of the genus Lactobacillus which has been recognized heretofore is shown as follows:

It is gram-negative, usually anaerobic and forms no spores. It's shape may be coccus-like, bended, coryne-like or thread-like, but not ramified significantly. It is non-motile, catalase negative and does not reduce nitrates. It does neither decompose gelatin nor produce indole and hydrogen sulfide. Some strains are bipolar-stained. The ability to decompose protein and fat is very weak, if any. It shows better growth under anaerobic or microaerophilic conditions rather than under aerobic conditions. It has potent ability to decompose sugar. It is acid-fast, and glucose-fermentation of the strains gives lactic acid in an yield of more than 50%. It is not pathogenic to both animals and plants.

Known Lactobacillus can grow only in a medium containing relatively good nutrients. Scientifically, this has been well-recognized as the nutritive requirements of Lactobacillus. Similarly, in the academic circle and in research there has been known no Lactobacillus microorganism which can squeeze into the established cluster of intestinal microbes or thrust aside other microbes thereby enabling itself to propagate and remain stable in the intestines for a lone time. As a matter of course, such Lactobacillus has not been isolated, collected and/or cultivated up to now.

Unlike those mentioned above, however, it has been found that Strain No. 1946/F.R.I. and other microorganisms isolated by the inventors can grow and propagate very well within a short time (e.g., 2 days) even under poor nutritional conditions, produce lactic acid, have the ability of deodorization, and further remain stable in the intestines. It has also been found that, when these microorganisms are administered to animals, the excrements discharged does not show it's peculiar odor and said loss of odor continues for a long time. Further, in addition to the microorganisms isolated by the inventors as having the ability to deodorize excrements for a long time, there were also isolated microorganisms which have the ability to deodorize excrements for (a) a fairly long time (about half a month), (b) a short time (about 5 to 10 days), (c) a considerably short time (about 2 to 3 days) as well as (d) microorganisms having the ability to reduce the odor of excrements for 2 to 7 days. The above-mentioned microorganisms of group (a) isolated by the inventors include Strain No. 2781/F.R.I. On the other hand, the microorganisms of group (b), (c) and (d) include Strain No. 2782/F.R.I., Strain No. 2779/F.R.I. and Strain No. 2780/F.R.I., respectively.

A rather high interrelation was recognized between the deodorizing ability and nutritive requirements of these microorganisms. Examples of said interrelation are shown in Tables 8 and 9.

All the properties of the Strain No. 1946/F.R.I. isolated by the inventors were identical with the aforementioned properties of Lactobacillus. Additionally, almost all of the microorganisms which showed the ability to deodorize raw excrements or a diluent thereof when cultivated therewith were identified to belong to the genus Lactobacillus. Moreover, as already mentioned in defining Lactobacillus, the shape of these microorganisms may vary such as rod-like, typical, oval rod-like or coccus-like. Further, it was recognized that some of these microorganisms change their shape to a remarkable extent by the difference of nutrients. For example, even the same microorganism changed its shape from rod-like to oval rod-like or coccus-like according to the medium employed. Accordingly, the microorganisms collected could not be classified into one or two species but covered a wide variety of Lactobacillus. Of those, the microorganisms belonging to *L. salivarius*, *L. acidophilus* and *L. delbruckii* were observed most frequently. On the other hand, 50% of the microorganisms could not be classified to any one of the known species. Besides, many strains having the productivity of antibiotics were also found among the isolated microorganisms.

Amino acids, peptides, nucleic acid analogs, vitamins, salts, fatty acids or their esters, sugars and so forth are required for the growth of Lactobacillus known heretofore. On the contrary, as will be seen in Tables 1 to 2, Lactobacillus isolated and collected by the inventors and which have the ability of deodorization need only remarkably poor nutrients. From this fact it is considered that the microorganisms isolated are a new group of Lactobacillus.

As for the biochemical properties of Lactobacillus employed in the present invention, those of the strain Strain No. 1946/F.R.I. are shown in Table 3 representatively.

Further, the living cells of the microorganism picked up by a loop or a culture broth of the microorganism were cultivated with four samples of animals' excrements, i.e., fresh and old excrements and their 5-fold diluents. The result of the experiments as to the decrease of odor of excrements are shown in Tables 1 to 5.

In this invention, the Strain No. 1946/F.R.I. and the like is the deposit number of the strains of this invention accepted by the Fermentation Research Institute (Agency of Industrial Science and Technology) of Japan.

TABLE 1

Relation between nutritive requirement and growth
Compounds added to the basic medium

| Microorganism | Basic medium | No addition | Sulfur-containing amino acid | Cyclic amino acid | Branched amino acid | Cystein | Cystine | Methionine | Casamino acid | Casamino acid + vitamin | Casamino acid + yeast extract | Yeast extract |
|---|---|---|---|---|---|---|---|---|---|---|---|---|
| Strain No. 1946/F.R.I. | (A) | — | +++ |   | + | ++ | ++ | + | ++ | ++ | ++ | ++ |
|  | (B) | — | + | + | — | + | + | + | + | ++ | ++ | ++ |

(A): S.W medium + agar
(B): S.W medium (agar was not added)
+: Growth in normal condition
++: Growth in the better condition
+++: Growth in the best condition
: Growth in the growing condition slightly
—: No growth S.W. medium components:
- $KH_2PO_4$ 1 g
- $MgSO_4 \cdot 7H_2O$ 0.7 g
- NaCl 1 g
- $(NH_4)_2HPO_4$ 4 g
- $FeSO_4 \cdot 7H_2O$ 0.03 g
- Glucose 5 g

TABLE 2

Relation between nutritive requirement and growth
Compounds added to the basic medium

| Microorganism | Basic medium | No addition | Acetic acid | Ammonia | Propionic acid | $Na_2S$ | Butyric acid | Skadol | Excrements juice |
|---|---|---|---|---|---|---|---|---|---|
| Strain No. 1946/ F.R.I. | A | — | — | — | — | — | — | — | + |
|  | B | — | — | — | — | ++ | — | + | + |
|  | C | + | + | — | — | ++ | ++ | + | ++ |
|  | D | + | ++ | — | — | ++ | ++ | + | ++ |

(A): S.W medium (No agar)
(B): S.W medium + agar
(C): Peptone 8 g; Glucose 2 g
(D): Peptone 10 g; Meat extract 5 g; NaCl 5 g; Glucose 1 g Components of S.W medium: They are identical with those disclosed in Table 1.

TABLE 3

| Properties | Microorganism | Strain No. 1946/F.R.I. |
|---|---|---|
| Microscopic observation | Shape | +<br>Short rod, non-spore-forming |
|  | Condition for cultivation | Usually anaerobic |
| Observation on medium | Shape of colony | It forms opaque white and moistened colinies on a glucose-agar medium with vitamin. The colony is of medium size. The surface of the colony is smooth and shows normal upheaval. |
| Biochemical properties | Catalase | — |
|  | Nitrate reduction | — |
|  | Gelatin liquefaction | — |
|  | Indole | — |
|  | Hydrogen sulfide | — |
|  | Ammonia production | — |
|  | Urea decomposition | — |
|  | Milk coagulation | — |

TABLE 3-continued

| Properties | Microorganism | Strain No. 1946/F.R.I. |
|---|---|---|
| Microscopic observation | Shape | +<br>Short rod, non-spore-forming |
|  | Condition for cultivation | Usually anaerobic |
|  | Motility | — |
|  | Hemolysis | — |
|  | Pigment production | — |
|  | Pathogenic property | — |
|  | Antibiotic productivity | + |

TABLE 4

| | Microorganism | Strain No. 1946/F.R.I. |
|---|---|---|
| Sugar decomposition | Ribose | — |
|  | Galactose | + |
|  | Sucrose | + |
|  | Maltose | + |
|  | Cellobiose | + |
|  | Lactose | + |
|  | Meliboise | + |
|  | Raffinose | — |
|  | Melecitose | — |
|  | Mannit | — |
|  | Gas production | — |

TABLE 5

Experiments as to deodorization of animal's excrements by Strain No. 1946/F.R.I. (Fresh excrements were employed)

| Animals employed | Fresh excrements (2 g in/total) (%) | (Control) No addition of micro- organisms | State of microorganisms added to excrements | | | | | |
|---|---|---|---|---|---|---|---|---|
| | | | Microbial cells (Clots of microbes) 3 loopful Period of cultivation after inoculation (hr.) | | | Culture broth cultivated for 48 hours (5 c.c) Period of cultivation after inoculation (hr.) | | |
| | | | 24 | 48 | 72 | 24 | 48 | 72 |
| Dogs | 100 | 4 | 2 | 2 | 1' | 2 | 2 | 1' |
| | 20 | 4 | 2' | 2 | 1' | 2 | 1' | 1' |
| Cows | 100 | 4 | 1' | 1' | 1' | 1 | 1' | 1 |
| | 20 | 4 | 1' | 1 | 1 | 2 | 2 | 1' |
| Pigs | 100 | 4 | 2 | 2 | 1' | 2' | 2 | 1' |
| | 20 | 4 | 2 | 2 | 1' | 2' | 2 | 1' |
| Chickens | 100 | 4 | 2 | 2 | 1' | 2' | 2 | 1' |
| | 20 | 4 | 2 | 2 | 1' | 2' | 2 | 1' |
| Human beings | 100 | 4 | 2' | 2 | 1' | 2' | 2 | 1' |
| | 20 | 4 | 2' | 2 | 1' | 2 | 2 | 1' |

TABLE 6

Experiments as to deodorization of animal's excrements by Strain No. 1946/F.R.I. (Old excrements were employed)

| Animals employed | Old excrements (2 g in/total) (%) | (Control) No addition of micro- organism | State of microorganisms added to excrements | | | | | |
|---|---|---|---|---|---|---|---|---|
| | | | Microbial cells (Clots of microbes) 3 loopful Period of cultivation after inoculation (hr.) | | | Culture broth cultivated for 48 hours (5 c.c.) Period of cultivation after inoculation (hr.) | | |
| | | | 24 | 48 | 72 | 24 | 48 | 72 |
| Dogs | 100 | 4 | 2 | 2 | 1 | 2' | 2 | 1' |
| | 20 | 4 | 2 | 2 | 1 | 2' | 2 | 1' |
| Cows | 100 | 4 | 2 | 1' | 1 | 2 | 1' | 1 |
| | 20 | 4 | 2 | 1' | 1 | 2 | 1' | 1 |
| Pigs | 100 | 4 | 2 | 2 | 1' | 2' | 2 | 1' |
| | 20 | 4 | 2 | 1' | 1' | 2' | 2 | 1' |
| Chickens | 100 | 4 | 2 | 2 | 1' | 2' | 2 | 2 |
| | 20 | 4 | 2 | 2 | 1' | 2' | 2 | 1' |
| Human beings | 100 | 4 | 2 | 2 | 1' | 2' | 2 | 1' |
| | 20 | 5 | 2 | 2 | 1' | 2 | 2 | 1' |

In Tables 5 to 6:
Excrements (%): 100% Excrements 100%
20% Excrements 20% Water 80%
Microbial cells: 3 loopful of the microorganism grown on a Petri dish were inoculated into the above-mentioned excrements.
Culture broth: 5 c.c of a broth of the microorganism grown well in a test tube were inoculated into the above-mentioned excrements.
Fresh excrements: Excrements just dishcarged.
Old excrements: Excrements elapsed 3 days after discharged.

1: No odor
1': Dim odor
2: Little odor is smelt initially, but will fade away sooner.
2': Little odor
3: The odor is less than that of the control group
3': The odor is dimly weaker than that of the control group.
4: The odor of excrements per se in the control group.

Whether the Lactobacillus strains can propagate in raw excrements and a diluent thereof is extremely important. In this respect, however, it is clear from Table 7 that the Lactobacillus strains can propagate very well in these materials.

TABLE 7

Degree of propagation of Strain No. 1946/F.R.I. in intestinal tract, fresh excrements, a diluent of fresh excrements and so forth

| Objects to be administered | Number of microorganisms at the time of inocula- tion (per 1 c.c) | Results obtained after inoculation of the strain (per 1 c.c) | | | |
|---|---|---|---|---|---|
| | | 24 hours | 48 hours | 72 hours | 96 hours |
| Intestines of human beings (Oral administration) | Those cultivated in 300 ml of a skim-milk medium (administered 2 times) | | $1 \times 10^9$ | $1.5 \times 10^9$ | $2 \times 10^9$ |
| Fresh excrements | $1 \times 10^8$ | $4 \times 10^8$ | $1 \times 10^9$ | $1.5 \times 10^9$ | $2 \times 10^9$ |
| A diluent of fresh excrements | $1 \times 10^8$ | $5 \times 10^8$ | $1 \times 10^9$ | $2 \times 10^9$ | $2 \times 10^9$ |
| Skim-milk medium | $1 \times 10^8$ | $6 \times 10^8$ | $3 \times 10^9$ | $5 \times 10^9$ | $5 \times 10^9$ |

In Table 7:
Intestines of human beings: 300 ml of a broth of the strain cultivated in a skim-milk medium were administered. Number of microbial cells in excrements was counted from the day after said administration.
Raw excrements: The strain was inoculated to fresh excrements just discharged, well mixed and cultivated for a period of time. Number of microbial cells was counted.
A diluent of fresh excrements: The strain was inoculated to a 5-fold diluent of excrements and cultivated for a period of time. Number of microbial cells was counted.
Skim-milk medium: Components of the medium -continued

```
┌ Skim-milk      60 g
│ Glucose        10 g
│ K₂HPO₄          2 g
⎨ Yeast extract   2 g
│ CaCO₃           3 g
└ pH             7.2
```

The strain Strain No. 1946/F.R.I. having the above-mentioned properties was cultivated in a nutrient medium to collect a large amount of the living cells thereof, and said living cells was then administered orally to animals. The deodorizing effect in this case are shown in Tables 8-1, 2 and -3.

In case of Table 8-1, the strain was cultivated in a nutrient medium containing skim-milk, sugar and CaCO₃. In case of Table 8-2, the strain was cultivated in a medium containing sugar and vitamin but not containing animal milk. In the latter case, the living cells was collected by a centrifuge under cooling, processed to make wet cake, mixed with (a) bread or (b) butter, and then administered orally. In case of Table 8-3, the above-mentioned wet cake was administered in admixture with drinking water.

Likewise, the living cells of the strain dispersed uniformly was mixed with a starch solution and then with dried materials such as dried starch, dried and further mixed with foods. Alternatively, the above-mentioned wet cake was mixed with a skim-milk solution containing lactose and then dried in vacuo, or said wet cake was mixed with foods. Oral administration of these products gave the same results as those obtained in the aforementioned cases.

TABLE 8-1

| Animals employed | Deodorizing effect and change thereof |
|---|---|
| Dogs | The deodorizing effect was observed on the 2nd day after the administration and continued for about 20 days. Thereafter, the excrements is started to emit its peculiar odor gradually and resumed its natural state. |
| Pigs | Same as above. |
| Chickens | The deodorizing effect was observed on the 2nd day after the administration and continued for about 15 days. Thereafter, the excrements is started to emit its peculiar odor gradually and resumed its natural state. |
| Human beings | Same as dogs' case. |

Note: Dogs: Mean Value of 50 dogs.
Pigs: Mean value of 20 pigs.
Chickens: Mean value of 30 chickens.
Human beings: Mean value of 15 men and 15 women.

TABLE 8-2

| Animals | Type | Deodorizing effect and change thereof |
|---|---|---|
| Dogs | (a) | The deodorizing effect was observed on the day after the administration and continued for about 40 days. Thereafter, the excrements is started to emit its peculiar odor gradually and resumed its natural state. |
| | (b) | The deodorizing effect was observed on the day after the administration and continued for about 45 to 50 days. Thereafter, the excrements is started to emit its peculiar odor gradually and resumed its natural state. |
| Pigs | (a) | The deodorizing effect was observed on the day after the administration and continued for about 30 days. It followed same as the dogs case above thereafter. |
| | (b) | The deodorizing effect was observed on the day after the administration and continued for about 40 days. It followed same as the dogs case above thereafter. |
| Chickens | (a) | The deodorizing effect was observed on the 2nd day after the administration and continued for about 20 days. It followed same as the dogs case above thereafter. |
| | (b) | The deodorizing effect was observed on the 2nd day after the administration and continued for about 20 days. It followed same as the dogs case above thereafter. |
| Human beings | (a) | Same as dogs case. |
| | (b) | Same as dogs case. |

TABLE 8-3

| Animals employed | Deodorizing effect and change thereof |
|---|---|
| Dogs | The deodorizing effect was observed on the 3rd day after the administration and continued for about 20 days. Thereafter, the excrement is started to emit its peculiar odor gradually and resumed its natural state. |
| Pigs | Same as above. |
| Chickens | The deodorizing effect was observed on the 3rd day after the administration and continued for about 15 days. Thereafter, the excrement is started to emit its peculiar odor gradually and resumed its natural state. |
| Human beings | Same as dogs. |

Further, it was confirmed that the strains of Lactobacillus which have the ability to deodorize fresh excrements or a diluent thereof involves various types of microorganisms. For example, some strains of this genus can deodorize excrements for a longer period of time (e.g., few months) than the strain Strain No. 1946/F.R.I. does. Additionally, the deodorizing effect or the duration of the deodorizing effect of some other strains may be influenced by foods.

TABLE 9

Relation between nutritive requirement and growth

| Micro-organisms | Basic medium | No addition | Sulfur-containing amino acid | Cyclic amino acid | Branched amino acid | Cystein | Cystine | Methionine | Casamino acid | Casamino acid + vitamin | Casamino acid + yeast extract | Yeast extract |
|---|---|---|---|---|---|---|---|---|---|---|---|---|
| Strain No. 2782/F.R.I. | A | − | + | − | + | ++ | + | + | + | + | + | + |
| | B | − | | + | + | | | | + | + | + | |
| Strain No. 2781/F.R.I. | A | − | + | + | + | + | ++ | + | + | ++ | ++ | + |
| | B | − | + | + | + | + | + | | + | ++ | ++ | + |
| Strain No. 2779/F.R.I. | A | − | + | − | + | − | − | + | + | + | + | + |
| | B | − | | + | + | − | − | | ++ | + | + | + |

TABLE 9-continued

Relation between nutritive requirement and growth
Compounds added to the basic medium

| Micro-organisms | Basic medium | No addition | Sulfur-containing amino acid | Cyclic amino acid | Branched amino acid | Cy-stein | Cy-stine | Methio-nine | Casa-mino acid | Casa-mino acid + vitamin | Casamino acid + yeast extract | Yeast extract |
|---|---|---|---|---|---|---|---|---|---|---|---|---|
| Strain No. 2780/F.R.I. | A | − | + | | + | − | − | − | | | + | + |
| | B | | | | − | − | − | | + | + | + | + |

NOTE:
The media were cultivated at 37°C for 48 hours.
A: Basic medium (S.W. medium) + Agar
B: Basic medium only. Agar was not added.

TABLE 10

Relation between nutritive requirement and growth
Compounds added to the basic medium

| Micro-organisms | Basic medium No addition | Acetic acid | Ammonia | Propionic acid | Na$_2$S | Butyric acid | Skadol | |
|---|---|---|---|---|---|---|---|---|
| Strain No. 2782/F.R.I. | A | − | ± | ± | ± | + | ± | + |
| | B | − | − | − | − | − | | + |
| Strain No. 2781/F.R.I. | A | − | + | + | + | + | + | + |
| | B | − | ++ | ++ | + | − | | + |
| Strain No. 2779/F.R.I. | A | − | ± | − | − | + | ± | − |
| | B | − | − | − | − | − | | − |
| Strain No. 2780/F.R.I. | A | − | − | − | − | − | − | |
| | B | − | − | − | − | − | − | |

Note:
The media were cultivated at 37°C for 24 hours.
A: Basic medium (S.W. medium) + Agar
B: Basic medium only. Agar was not added.

A practical embodiment of the present invention is shown in the following lines.

EXAMPLE 10 g of the strain No. 1946/F.R.I. were inoculated to 18 l of a medium containing vitamin and 60 g/l of skim-milk, or to 18 l of boullion containing vitamin. The medium or boullion was cultivated at 37°C for 3 days, and the living cells of the strain was collected by centrifugation under cooling. 30 g of the living cells were administered to a dog, and the odor change of excrements was examined. As a result it was observed that the dog's excrements was deodorized remarkably for about 40 days from the 2nd day of the administration.

On the other hand, 3 loopful of the strain was inoculated to 2 g of fresh excrements charged into a test tube, and cultivated therein at 37°C for 3 days. In this case, the remarkable deodorizing effect was also observed.

What is claimed is:

1. A method for deodorization of excrements of human beings or animals which comprises administering to said human beings or animals the living cells of a microorganism selected from the group consisting of:
   a. Lactobacillus F.R.I. Strain No. 1946;
   b. Lactobacillus F.R.I. Strain No. 2779,
   c. Lactobacillus F.R.I. Strain No. 2780,
   d. Lactobacillus F.R.I. Strain No. 2781 and
   e. Lactobacillus F.R.I. Strain No. 2782.

2. A method for the deodorization of excrements of human beings or animals as claimed in claim 1, wherein said microorganism is Lactobacillus F.R.I. Strain No. 1946.

3. A method for the deodorization of excrements of human beings or animals, as claimed in claim 1, wherein said microorganism is Lactobacillus F.R.I. Strain No. 2779.

4. A method for the deodorization of excrements of human beings or animals as claimed in claim 1, wherein said microorganism is Lactobacillus F.R.I. Strain No. 2780.

5. A method for the deodorization of excrements of human beings or animals as claimed in claim 1 wherein said microorganism is Lactobacillus F.R.I. Strain No. 2781.

6. A method for the deodorization of excrements of human beings or animals as claimed in claim 1 wherein said microorganism is Lactobacillus F.R.I. Strain No. 2782.

7. A method according to claim 1 wherein the microorganism is administered to human beings.

* * * * *